United States Patent
Heldreth, Jr.

(10) Patent No.: US 12,274,210 B2
(45) Date of Patent: Apr. 15, 2025

(54) PRODUCTION AND USE OF THE LEAF AND/OR LEAVES AND/OR STEM(S) AND/OR STALK(S) OF PLANTS OF THE CANNABIS SPECIES FOR CONSUMPTION AS A FOOD, BEVERAGE INGREDIENT, SUPPLEMENT, MEDICINE

(71) Applicant: David Alan Heldreth, Jr., Bellevue, WA (US)

(72) Inventor: David Alan Heldreth, Jr., Bellevue, WA (US)

( * ) Notice: Subject to any disclaimer, the term of this patent is extended or adjusted under 35 U.S.C. 154(b) by 97 days.

(21) Appl. No.: 17/689,706

(22) Filed: Mar. 8, 2022

(65) Prior Publication Data

US 2023/0116837 A1 Apr. 13, 2023

Related U.S. Application Data

(60) Provisional application No. 63/207,568, filed on Mar. 8, 2021.

(51) Int. Cl.
| | | |
|---|---|---|
| *A01G 22/15* | (2018.01) | |
| *A01C 7/00* | (2006.01) | |
| *A01D 45/06* | (2006.01) | |
| *A23L 2/52* | (2006.01) | |
| *A23L 29/00* | (2016.01) | |
| *A24B 15/16* | (2020.01) | |
| *A24B 15/167* | (2020.01) | |
| *A61K 36/185* | (2006.01) | |
| *C12G 3/04* | (2019.01) | |

(52) U.S. Cl.
CPC ............ *A01G 22/15* (2018.02); *A01C 7/00* (2013.01); *A01D 45/065* (2013.01); *A23L 2/52* (2013.01); *A23L 29/00* (2016.08); *A24B 15/16* (2013.01); *A24B 15/167* (2016.11); *A61K 36/185* (2013.01); *C12G 3/04* (2013.01); *A61K 2236/13* (2013.01); *A61K 2236/15* (2013.01)

(58) Field of Classification Search
None
See application file for complete search history.

(56) References Cited

FOREIGN PATENT DOCUMENTS

WO WO 2021/087314 * 5/2021

OTHER PUBLICATIONS

Kleinhenz et al. Applied Animal Science, 36, 489-494, 2020.*

* cited by examiner

*Primary Examiner* — Michael V Meller

(57) ABSTRACT

This present invention is directed to a method for the production and use of the leaf and/or leaves and/or stem(s) and/or stalk(s) of plants of the cannabis species for animal, microbial, bacteria, fungi or human consumption as a food, supplement, medicine, beverage.

4 Claims, 1 Drawing Sheet

| | |
|---|---|
| Fig. 1 | Cultivate Cannabis plants (indoor, greenhouse, outdoor, field) |
| Fig. 2 | Harvest cannabis leaves and/or stems and/or stalks prior to flowering |
| Fig. 3 | Washing/Rinsing process |
| Fig. 4 | processing, preparation for packaging under CGMP/FDA guidance |
| Fig. 5 | Sorting cannabis leaves/stems/stalks by quality and/or use |
| Fig. 6 | Mixing cannabis leaf/stems/stalks with food/additives etc |
| Fig. 7 | Packing/Packaging for transport/shipping/sale/consumption |

PRODUCTION AND USE OF THE LEAF AND/OR LEAVES AND/OR STEM(S) AND/OR STALK(S) OF PLANTS OF THE CANNABIS SPECIES FOR CONSUMPTION AS A FOOD, BEVERAGE INGREDIENT, SUPPLEMENT, MEDICINE

This patent claims priority to USPTO provisional patent filing US202163207568P which was filed by the inventor on Mar. 8, 2021 and entitled The production and use of the leaf and/or leaves and/or stem(s) and/or stalk(s) of plants of the cannabis species for consumption as a food, beverage ingredient, supplement, medicine.

DESCRIPTION

Field of the Invention

This present invention is directed to a method for the production and use of the leaf and/or leaves and/or stem(s) and/or stalk(s) of plants of the cannabis species for animal, microbial, bacteria, fungi or human consumption as a food, supplement, medicine.

Background of the Invention

The cannabis plant has been cultivated for thousands of years for a variety of uses from the seed for food use as a seed oil, raw seed, extracted seed protein. It has also been used as a medicine by taking the cannabinoids and other compounds out of the plant. However, there has been little to no use of the whole plant parts of the cannabis plant, especially beyond the cannabis flower. The primary use previously described for the cannabis leaf and stalk are for juicing, however this method requires heavy processing and does separates the whole plant parts into different components. The whole plant parts contain a synergy of nutrition and medical value which is not accessible through separation and reconstitution.

As such we now present a complete system of production and use of the leaf and/or leaves and/or stem(s) and/or stalk(s) of plants of the cannabis species prior to flowering.

SUMMARY OF THE INVENTION

This present invention is directed to a method for the production and use of the leaf and/or leaves and/or stem(s) and/or stalk(s) of plants of the cannabis species prior to flowering for animal, microbial, bacteria, fungi or human consumption as a food, beverage ingredients, supplement, medicine.

BRIEF DESCRIPTION OF THE DRAWINGS

The drawing shows one embodiment of the invention in which the cannabis follows this process flow from:

FIG. 1: Cultivating cannabis; to

FIG. 2: harvesting cannabis leaf and/or leaves and/or stem(s) and/or stalk(s) prior to flowering; to FIG. 3: rinsing and/or chilling and/or washing and/or the cannabis leaf and/or leaves and/or stem(s) and/or stalk(s) either during harvest/within 12 hours of harvest; to FIG. 4: further preparing the cannabis leaf and/or leaves and/or stem(s) and/or stalk(s) for packaging according to current good manufacturing processes (CGMP) and/or FDA guidance; to FIG. 5: sorting the cannabis leaf and/or leaves and/or stem(s) and/or stalk(s) into plant parts and/or by quality and/or by intended use;

FIG. 6: Mixing cannabis leaf and/or leaves and/or stem(s) and/or stalk(s) with any single item or a mixture of items from this list: food ingredients, food additives, supplements, medicines, preservatives, essential oils, flavors, nano technology, encapsulation, beta glucan particles, chitosan, yeast extract, surfactants, binders and other compounds to increase efficiency, availability, release lifespan, release speed among other parameters; and finally to FIG. 7: packing/packaging for transport and/or shipping and/or manufacturing and/or sale and/or consumption.

DRAWING SUMMARY

The drawing shows one embodiment of the invention in which the cannabis follows this process flow from:

FIG. 1: Cultivating cannabis; to

FIG. 2: harvesting cannabis leaf and/or leaves and/or stem(s) and/or stalk(s) prior to flowering; to FIG. 3: rinsing and/or chilling and/or washing and/or the cannabis leaf and/or leaves and/or stem(s) and/or stalk(s) either during harvest/within 12 hours of harvest; to FIG. 4: further preparing the cannabis leaf and/or leaves and/or stem(s) and/or stalk(s) for packaging according to current good manufacturing processes (CGMP) and/or FDA guidance; to FIG. 5: sorting the cannabis leaf and/or leaves and/or stem(s) and/or stalk(s) into plant parts and/or by quality and/or by intended use;

FIG. 6: Mixing cannabis leaf and/or leaves and/or stem(s) and/or stalk(s) with any single item or a mixture of items from this list: food ingredients, food additives, supplements, medicines, preservatives, essential oils, flavors, nano technology, encapsulation, beta glucan particles, chitosan, yeast extract, surfactants, binders and other compounds to increase efficiency, availability, release lifespan, release speed among other parameters; and finally to FIG. 7: packing/packaging for transport and/or shipping and/or manufacturing and/or sale and/or consumption.

DETAILED DESCRIPTION OF THE INVENTION

This present invention is directed to a method for the production and use of the leaf and/or leaves and/or stem(s) and/or stalk(s) of plants of the cannabis species for animal, microbial, bacteria, fungi or human consumption as a food, supplement, medicine.

In one embodiment the method includes the any mixture of the following steps: (a) harvesting cannabis leaf and/or leaves and/or stem(s) and/or stalk(s) prior to flowering; (b) rinsing and/or chilling and/or washing and/or the cannabis leaf and/or leaves and/or stem(s) and/or stalk(s) either during harvest/within 12 hours of harvest; (c) further preparing the cannabis leaf and/or leaves and/or stem(s) and/or stalk(s) for packaging according to current good manufacturing processes (CGMP) and FDA guidance; (d) sorting the cannabis leaf and/or leaves and/or stem(s) and/or stalk(s) into plant parts and/or by quality and/or by intended use; and (e) packing/packaging for transport and/or shipping and/or sale and/or consumption.

In one embodiment the cannabis leaf and/or leaves and/or stem(s) and/or stalk(s) are organically grown. In one embodiment the cannabis leaf and/or leaves and/or stem(s) and/or stalk(s) are grown indoors. In one embodiment the cannabis leaf and/or leaves and/or stem(s) and/or stalk(s) are grown outdoors. In one embodiment the cannabis leaf and/or leaves and/or stem(s) and/or stalk(s) are grown in a greenhouse. In one embodiment the cannabis leaf and/or leaves and/or stem(s) and/or stalk(s) are grown in a field. In one embodiment the cannabis leaf and/or leaves and/or stem(s) and/or stalk(s) are grown hydroponically. In one embodiment the cannabis leaf and/or leaves and/or stem(s) and/or stalk(s) are grown aeroponically. In one embodiment the cannabis leaf and/or leaves and/or stem(s) and/or stalk(s) are grown with conventional nutrients. In one embodiment, the cannabis leaf and/or leaves and/or stem(s) and/or stalk(s) are harvested simultaneously from the same plant to reduce harvest time, labor, cost and potential contamination from individually collecting leaf and/or leaves, stem(s) or stalk(s) from plants. In one embodiment the cannabis leaf and/or leaves and/or stem(s) and/or stalk(s) are harvested utilizing mechanical harvesting equipment such as, but not limited to combines or spinach/microgreen/spring mix harvesters such as made by companies: Ramsay, Tumoba, Ortomec.

In one embodiment the cannabis leaf and/or leaves and/or stem(s) and/or stalk(s) are used as whole plants. In one embodiment the cannabis leaf and/or leaves and/or stem(s) and/or stalk(s) are ground to be mixed into foods. In one embodiment the cannabis leaf and/or leaves and/or stem(s) and/or stalk(s) are separated after harvest. In one embodiment the cannabis leaf and/or leaves and/or stem(s) and/or stalk(s) are sorted utilizing artificial intelligence and/or visual/infrared/density and other scanners. In some embodiment the cannabis leaf and/or leaves and/or stem(s) and/or stalk(s) are consumed raw. In some embodiment the cannabis leaf and/or leaves and/or stem(s) and/or stalk(s) are cooked. In some embodiment the cannabis leaf and/or leaves and/or stem(s) and/or stalk(s) are frozen. In some embodiments the cannabis leaf and/or leaves and/or stem(s) and/or stalk(s) are dehydrated. In some embodiment the cannabis leaf and/or leaves and/or stem(s) and/or stalk(s) are used individually.

In some embodiments the cannabis contains below 0.3% total delta-9tetrahydrocannabinol (D9THC) content as calculated as Total D9THC=(0.877*% D9THC-acid)+% D9THC. In some embodiments the cannabis contains below 0.3% total (THC) in which this calculation includes a total of all tetrahydrocannabinol isomers and analogs such as, but not limited to delta-8-tetrahydrocannabinol, delta-10tetrahydrocannabinol, 11-hydroxy-tetrahydrocannabinol as required by the FDA, DEA or other government agency.

Some embodiments will include utilizing nano technology, encapsulation, beta glucan particles, chitosan, yeast extract, surfactants, binders and other compounds to increase efficiency, availability, release lifespan, release speed among other parameters.

In some embodiments cannabis leaf and/or leaves and/or stem(s) and/or stalk(s) are used in foods, supplements, inhalation products such as, but not limited to: vaporizers, cigarettes, cigars, infused smoking papers, infused smoking blends, cigarillos, vape fluids, eye drops, nasal spray, mouth spray, rectal inhalers or other uses.

Some embodiments are used to develop vaccines or treatments for virus, fungi or bacteria illness such as, but not limited to: Coronavirus (such as SARS, COVID-19, MERS), HIV, herpes, syphilis, flu virus, swine flu, avian flu, other virus, bacteria or fungi: antibodies-cytokins-proteins-amino acids-DNA-RNA-DNA/RNA to produce antibodies/proteins/amino acids/RNA/DNA; such as for the spike or other proteins used in vaccines or treatment of virus, fungi or bacteria illness.

The invention claimed is:

1. A method for preparing a pre-packaged cannabis leaf food product consisting of:
   a. cultivating cannabis which has more than 7% wt. % protein in the entire cannabis leaf;
   b. harvesting the cannabis prior to flowering;
   c. rinsing, chilling and/or washing the cannabis either during the harvest or within 12 hours of the harvest;
   d. sorting the cannabis leaf/leaves from the rest of the cannabis;
   e. mixing the cannabis leaves/leaf with a mixture of spinach, arugula, lettuce, carrots, mustard greens, tomatoes, and beets; or Chervil, arugula, lettuce, endive, chive, mustard greens, dandelion, and mizuna; or Lettuce, spinach, carrots, radicchio, broccoli, cauliflower, cucumber, and celery to form a cannabis leaf food product; and
   f. packaging the cannabis leaf food product with topping/dressing for transportation and/or for sale in a bag or box or plate/bowl, wherein the total THC level in the cannabis is below 0.3%.

2. The method of claim 1, further consisting of an item selected from the group consisting of salt, pepper, basil, oregano, rosemary, clove, mustard, mustard seed(s), dill, fennel, cannabis/hemp flower(s), cannabis/hemp seed(s), cucumber(s), carrot(s), olive(s), caper(s), tomato(es), olive oil, pepper(s), lettuce, spinach, bacon, ham, chicken, beef, pork, egg(s), cheese(s), cabbage, dandelion, mizuna, chervil, arugula, lettuce, endive, chive, mustard greens, broccoli, cauliflower, tortilla, pumpkin seeds, cilantro, peppitas, kale, radish, green onion, onion, almonds, wonton(s), crispy wontons, brussel sprouts, lemon, olive oil, and pickles.

3. The method of claim 1, wherein the cannabis leaf food product is pasteurized or cooked.

4. The method of claim 1, further consists of a preservative selected from the group consisting of sodium benzoate, potassium sorbate, sulfur dioxide, rosemary oil, vitamin e and vitamin c.

* * * * *